United States Patent [19]

Storhoff et al.

[11] Patent Number: 5,583,006
[45] Date of Patent: Dec. 10, 1996

[54] STABILIZING TETRAZOLIUM SALTS IN A REAGENT

[75] Inventors: Diana F. Storhoff, Muncie; David Tabb, Greenfield, both of Ind.

[73] Assignee: Boehringer Mannheim Corporation, Indianapolis, Ind.

[21] Appl. No.: 434,113

[22] Filed: May 4, 1995

Related U.S. Application Data

[63] Continuation of Ser. No. 908,127, Jul. 2, 1992, abandoned.

[51] Int. Cl.[6] .............................. C12Q 1/54; C12Q 1/00; C12Q 1/28; G01N 33/48
[52] U.S. Cl. ..................... 435/14; 435/4; 435/28; 435/25; 435/15; 435/26; 436/63; 436/800; 436/74
[58] Field of Search ................... 435/14, 4, 28, 435/25, 15, 26; 436/63, 800, 74

[56] References Cited

U.S. PATENT DOCUMENTS

| | | | |
|---|---|---|---|
| H622 | 4/1989 | Kageyama et al. | 435/14 |
| 3,732,147 | 5/1973 | Fosker et al. | 422/56 |
| 4,042,392 | 8/1977 | Gysling et al. | 430/417 |
| 4,247,633 | 1/1981 | Case et al. | 435/14 |
| 4,427,771 | 1/1984 | Misaki et al. | 435/22 |
| 4,476,222 | 10/1984 | Ohtani et al. | 435/14 |
| 4,645,742 | 2/1987 | Baker | 436/15 |
| 4,743,559 | 5/1988 | Koéver et al. | 435/28 |
| 4,748,115 | 5/1988 | Steaffens | 435/21 |
| 4,892,817 | 1/1990 | Pawlak | 435/21 |
| 4,946,776 | 8/1990 | Ritterband | 435/21 |
| 5,036,000 | 7/1991 | Palmer et al. | 435/10 |
| 5,126,247 | 6/1992 | Palmer et al. | 435/26 |
| 5,126,275 | 6/1992 | Hatch et al. | 435/25 |

OTHER PUBLICATIONS van Noorden CJ et al; Acta Histochem Suppl, vol. 24 pp. 231–236 (1981) "Quantitative aspects of the Cytochem Demonstration G–6PDH with Tetrazolium Salts Studied in a Model System of Polyacrylamide Films.".

*Primary Examiner*—John Kight
*Assistant Examiner*—Louise N. Leary
*Attorney, Agent, or Firm*—D. Michael Young

[57] ABSTRACT

A stable reagent for assaying an analyte from a fluid sample which includes an enzyme, a mediator, a tetrazolium salt and an oxidizing agent selected from the group consisting of sodium chlorate, 2,5-dimethylhexane-2,5-dihydroperoxide, benzoyl peroxide, t-butyl peroxide, sodium iodate, N-ethylmaleimide, t-butylperoxyacetate, nickel acetylacetonate, stannic chloride, rhodium (III) trichloride hydrate, and t-butylperbenzoate is described. Inclusion of an oxidizing agent from the group specified above stabilizes the reagent, thereby preventing a high blank reaction because a high blank introduces error into the assay of an analyte. The reagent may be provided in solution form by adding water, or may be included in a film by adding a film-forming agent. The reagent may be utilized to perform the assay of an analyte from a fluid sample. The assay may be conducted in a solution medium by adding the fluid sample to the liquid reagent, and spectrophotometrically measuring absorbance of the color indicating the presence of formazan which was produced by reduction of the tetrazolium salt under assay conditions. Alternatively, the assay may be conducted in a film medium by adding the fluid sample to the reagent incorporated in the film, and spectrophotometrically measuring reflectance or transmittance of the color indicating formazan.

20 Claims, No Drawings

STABILIZING TETRAZOLIUM SALTS IN A REAGENT

This is a continuation of application Ser. No. 07/908,127 filed on Jul. 2, 1992, now abandoned.

FIELD OF THE INVENTION

The invention relates to the colorimetric assay of an analyte from a fluid sample, wherein the reagent utilized for assay includes a tetrazolium salt.

BACKGROUND OF THE INVENTION

The colorimetric assay of an analyte from a fluid sample by utilizing a reagent that includes a tetrazolium salt is well known. Schematically, such assay is exemplified as shown immediately below (exemplified for glucose assay):

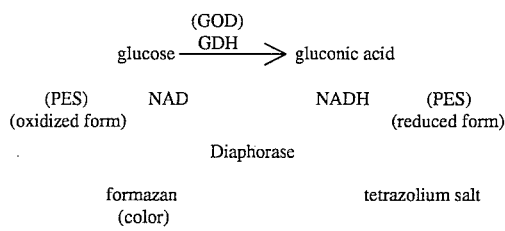

In the above example, glucose is catalytically oxidized by glucose dehydrogenase (GDH) to gluconic acid. As glucose is oxidized, a mediator, nicotinamide adenine dinucleotide (NAD) is reduced (NADH). A second enzyme, diaphorase, reoxidizes NADH to NAD and reduces the tetrazolium salt to a colored formazan. Alternatively, the enzyme involved in catalytic oxidation of glucose may be glucose oxidase (GOD), and the mediator may be phenazine ethosulfate (PES) (see schematic above). (When GOD is the enzyme involved in glucose oxidation, the second enzyme, diaphorase, is not required for the assay. PES (reduced form) will reduce the tetrazolium salt to the colored formazan, thereby reoxidizing PES.)

The use of tetrazolium salts in a reagent for the assay of an analyte in a fluid sample is disclosed in Baker, U.S. Pat. No. 4,645,742, issued Feb. 24, 1987, Hidehiko et al., U.S. Pat. No. 4,427,771, issued Jan. 24, 1984, and Case et al., U.S. Pat. No. 4,247,633, issued Jan. 27, 1981.

Koëver et al., U.S. Pat. No. 4,743,559, issued May 10, 1988, discloses the incorporation of iodate in a reagent test strip that includes a tetrazolium salt. Iodate is added to oxidize ascorbic acid and remove it as an interferrent in assays that involve oxidation-reduction reactions.

Pawlak, U.S. Pat. No. 4,892,817, issued Jan. 9, 1990, discloses moderate stabilization of tetrazolium salt solutions by addition of potassium permanganate, and manganese dioxide. Pawlak does not provide any reagent formulations that include these oxidizing agents, but merely lists in Table 2 of Pawlak that moderate stabilization is achieved in a few cases.

None of these references discloses a reagent that includes a tetrazolium salt and further includes the oxidizing agents (disclosed below), which are useful for stabilizing the reagent, thereby decreasing the blank reaction observed in assays utilizing reagents that include a tetrazolium salt.

SUMMARY OF THE INVENTION

The invention is a stable reagent for the assay of an analyte from a fluid sample. The reagent includes an enzyme, a mediator, a tetrazolium salt and an oxidizing agent selected from the group consisting of sodium chlorate, 2,5-dimethylhexane- 2,5-dihydroperoxide (sold under the trademark "LUPEROX" and available from Atochem), benzoyl peroxide, t-butyl peroxide, sodium iodate, N-ethylmaleimide, t-butylperoxyacetate, nickel acetylacetonate, stannic chloride, rhodium (III) trichloride hydrate, and t-butylperbenzoate.

Importantly, inclusion of an oxidizing agent from the group specified above stabilizes the reagent, thereby preventing a high blank reaction (which introduces error into the assay of an analyte).

The reagent may be provided in solution form by adding water, or may be included in a film by adding a film-forming agent.

The reagent may be utilized to perform the assay of an analyte from a fluid sample. The assay may be conducted in a solution medium by adding the fluid sample to the liquid reagent, and spectrophotometrically measuring absorbance of the color-indicating formazan (produced by reduction of the tetrazolium salt under assay conditions). Likewise, the assay may be conducted in a film medium by adding the fluid sample to the reagent incorporated in the film, and spectrophotometrically measuring reflectance or transmittance of the color-indicating formazan.

DETAILED DESCRIPTION OF THE INVENTION

The inventive reagent for the assay of an analyte from a fluid sample must include an enzyme, a mediator (that is, an oxidation-reduction mediator), a tetrazolium salt, and an oxidizing agent.

The enzyme must be of sufficient type and in sufficient amount to catalyze a reaction involving enzyme, analyte, and mediator. For example, when glucose is the analyte being measured, the enzyme glucose oxidase will catalyze the reaction shown below:

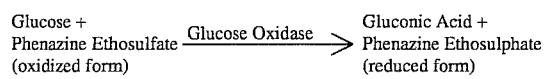

The mediator utilized must be of sufficient type and in sufficient amount to catalyze reduction of the tetrazolium salt. Phenazine ethosulfate exemplifies the type of mediator that may be used. As shown below, the reduced form of phenazine ethosulfate reacts with the tetrazolium salt, thereby reducing the tetrazolium salt to its colored formazan and reoxidizing phenazine ethosulfate.

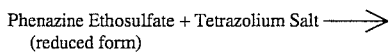

Formazan + Phenazine Ethosulfate (oxidized form)

The tetrazolium salt must be of sufficient type to be reduced to a colored formazan, and must be in sufficient amount to correlate the concentration of formazan to the concentration (or detection) of analyte in the fluid sample. Examples of tetrazolium salts that may be used include 3-(4,5-dimethylthiazol-2-yl)-2,5-diphenyltetrazolium bromide (MTT); p-iodonitrotetrazolium violet (INT); nitro blue tetrazolium chloride (NBT); tetranitro blue tetrazolium chloride (TNBT); tetrazolium blue; tetrazolium violet; thiocarbamyl nitro blue tetrazolium chloride; and triphenyltetrazolium chloride.

Importantly, the oxidizing agent stabilizes the reagent, thereby minimizing the blank reaction (premature formation of formazan) observed when conducting the assay of an analyte. The oxidizing agent is selected from the group consisting of sodium chlorate, 2,5-dimethylhexane-2,5-dihydroperoxide, benzoyl peroxide, t-butylperoxide, sodium iodate, N-ethylmaleimide, t-butylperoxyacetate, nickel acetylacetonate, stannic chloride, rhodium (III) trichloride hydrate, t-butylperbenzoate. Further, the oxidizing agent must be in sufficient amount to decrease the presence of formazan in the reagent prior to combining the fluid sample and the reagent.

The reagent may be provided in liquid form by adding water in sufficient amount to form a solution, or the reagent may be incorporated into a film by adding a film-forming agent in sufficient amount to form a cohesive film. When the reagent is supplied in a film, from about 0.4 to about 3 millimoles (mmol) of oxidizing agent per gram (g) of wet reagent will be sufficient to stabilize the film. Below about 0.4 mmol of oxidizing agent per gram of wet reagent, the reagent will be unsatisfactorily stabilized. More than about 3 mmol of oxidizing agent per gram of wet reagent may denature the enzyme in the reagent. The amounts of enzyme, mediator, and tetrazolium salt utilized in a reagent in order to perform the assay of an analyte from a fluid sample, such as serum or whole blood, are well known to those of ordinary skill in the art.

Results achieved in stabilizing tetrazolium salts in a liquid reagent or in a film are listed below in Table 1.

2. 3.0 g of 3% (by weight) methyl-hydroxyethyl cellulose, MHB grade, sold under the trademark "TYLOSE", (available from American Hoechst Corp., Speciality Products Group) in aqueous 0.3 molar (M) N-2-hydroxyethylpiperazinepropanesulphonic acid (HEPPS) buffer;
3. 0.5 g of 5% (by weight) aqueous polyoxyethylene ethers and other surface-active compounds, sold under the trademark "TRITON X-100" (a surfactant), available from Fisher Scientific and from Sigma Chemical Company;
4. 10.0 g of a 51.9% (by weight) aqueous silica composition, having 10.04 g of 3% (by weight) aqueous methyl-hydroxyethyl cellulose, 5.98 g of 5% (by weight) aqueous "TRITON X-100" surfactant, 121.74 g water, 62.95 g silica, sold under the trademark "CROSSFIELD WP", and 85.48 g silica, sold under the trademark "NEOSYL ET" (both silicas are available from Crossfield Chemical);
5. 3.1 g of styrene acrylic latex emulsion polymer, a film-forming agent, sold under the trademark "UCAR 455", available from Union Carbide;
6. 0.14 g of sodium chloride; and
7. 0.04 g of glycerol.

The above-stated components were mixed together and the resulting composition was adjusted to pH=7.9 by the addition of sodium hydroxide. Next, the following components were added in the following amounts: 66 milligrams (mg) diaphorase, 1.82 g oxidizing agent, and 368 mg MTT, thereby yielding a wet reagent mixture. (Diaphorase was from BMB Research and contained about 15 Units of enzyme per milligram (mg) of material.)

TABLE 1

| Analytical System | Oxidizing Agent | Reagent Medium | % Decrease in Blank Reaction |
| --- | --- | --- | --- |
| Diaphorase/MTT | sodium chlorate | Reflectance film | 100 (after 5 days) |
| | benzoyl peroxide | | 10 |
| | 2,5-dimethylhexane-2,5-dihydroperoxide | | 10 |
| GDH/NAD/Diaphorase/MTT | sodium chlorate + 2,5-dimethylhexane-2,5-dihydroperoxide | Reflectance film | 100 (after 15 days) |
| GOD/PES/MTT | sodium chlorate | Reflectance film | 100 (after 5 days) |
| | sodium chlorate + benzoyl peroxide | | 100 (after 5 days) |
| | t-butyl peroxide | | 100 (after 4 days) |
| | 2,5-dimethylhexane-2,5-dihydroperoxide | | 15–20 |
| | sodium iodate | | visually observed some decrease in blank reaction |
| | N-ethylmaleimide | | visually observed some decrease in blank reaction |
| GOD/PES/MTT | nickel acetylacetonate | Transmission film | visually observed decrease in blank reaction |
| | stannic chloride | | visually observed decrease in blank reaction |
| | rhodium (III) trichloride hydrate | | visually observed decrease in blank reaction |
| GOD/PES/MTT | t-butylperbenzoate | Aqueous reagent | visually observed slight decrease in blank reaction |
| | t-butylperoxyacetate | | visually observed slight decrease in blank reaction |

The reagent used in the Diaphorase/MTT analytical system (Table 1) was formulated in the following relative proportions:
1. 5.0 grams (g) of 15% (by weight) aqueous polyvinyl alcohol (88% hydrolyzed, average molecular weight=10,000, a film-forming agent available from Aldrich Chemical Company, Inc.);

The wet reagent mixture was coated by a blade coater at 50 microns (μm) thickness onto a titanium dioxide reflectance film, which was previously coated onto a web made of polyester (Web 777 from SST in Switzerland). Drying the wet reagent at 40° C. for 10 minutes produced a dried, reagent coated reflectance film.

The titanium dioxide film, which was coated onto the web (mentioned in the previous paragraph) was made with the following ingredients:
1. 2.90 g of 0.5% (by weight) aqueous methyl-hydroxyethyl cellulose;
2. 4.32 g of 0.3M aqueous HEPPS buffer at pH=7.9;
3. 2.11 g of 5% (by weight) aqueous "TRITON X-100" surfactant;
4. 2.28 g of a solvent mixture of 3 parts (by weight) acetone, 2 parts (by weight) hexanol, and 1 part (by weight) methanol;
5. 3.47 g water;
6. 3.43 g vinyl acetate homopolymer, sold under the trademark "VINAC XX 240", available from Air Products;
7. 3.83 g of silica, sold under the trademark "HI-SIL", available from PPG Industries; and
8. 5.64 g of titanium dioxide, sold under the trademark "ZOPAQUE RCL2", available from SCM Corporation in Baltimore, Md.

The above ingredients formed a slurry, which was mixed at 200 revolutions per minute (rpm) on a Heidolph mixer overnight, then mixed at 400 rpm for 45 minutes. The resulting wet titanium dioxide reflectance film was coated at 200 μm thickness with a blade coater onto the web made of polyester and dried at 60° C. for 30 minutes.

After the reagent was dried onto the titanium dioxide film, reflectance of the reagent coated film was spectrophotometrically measured at 560 nanometers (nm).

The spectrophotometric reflectance measurement of the reagent coated film was compared to the spectrophotometric reflectance measurement of a control reagent coated film, which was made in the same manner as the reagent coated film but without oxidizing agent. The percentage increase in spectrophotometric reflectance of the reagent coated film over the control reagent coated film is shown in Table 1 as the % decrease in blank reaction, which resulted from incorporating the oxidizing agent in the reagent.

When the oxidizing agent was sodium chlorate, the comparison was made between a reagent coated film that was 5 days old and a freshly made control reagent coated film without oxidizing agent. Further, although Table 1 shows a more stable reagent was achieved with sodium chlorate than with benzoyl peroxide, later experiments showed benzoyl peroxide to be superior to sodium chlorate for stabilizing the reagent in a film.

The reagent used in the GDH (glucose dehydrogenase)/NAD (nicotinamide adenine dinucleotide)/diaphorase/MTT analytical system (see Table 1) was formulated similarly to the diaphorase/MTT reagent as follows:
1. 5.03 g of 15% (by weight) aqueous polyvinyl alcohol (88% hydrolyzed, average molecular weight=10,000, a film-forming agent available from Aldrich Chemical Company, Inc.);
2. 3.0 g of 3% (by weight) methyl-hydroxyethyl cellulose in aqueous 0.3M HEPPS buffer;
3. 0.51 g of 5% (by weight) aqueous "TRITON X-100" surfactant;
4. 10.15 g of the 51.9% (by weight) aqueous silica composition (having the same composition as 4. above in the description of the reagent for the Diaphorase/MTT analytical system);
5. 3.15 g of styrene acrylic latex emulsion polymer, sold under the trademark "UCAR 455";
6. 0.1462 g sodium chloride; and
7. 0.0362 g glycerol.

Also added were 1.78 g sodium chlorate and 1.59 g 2,5-dimethylhexane-2,5-dihydroperoxide oxidizing agents.

The above components were mixed and the pH was adjusted to 8.0 by the addition of sodium hydroxide, thereby forming a resulting composition.

To 12.05 g of the resulting composition, 37.3 mg diaphorase, 44.7 mg GDH, and 94.0 mg NAD were added, followed by mixing, thereby forming a mixture. (GDH was from United States Biochemicals and contained about 200 of Units of enzyme per mg of material.) Finally, 63.20 mg MTT was added to 4.01 g of the mixture, followed by mixing, thereby forming wet reagent. Wet reagent was coated onto the titanium dioxide reflectance film, which was previously coated onto the web made of polyester, as specified above for the reagent coated film of the Diaphorase/MTT analytical system. Drying the wet reagent at 40° C. for 10 minutes produced a dried, reagent coated reflectance film. Fifteen days after drying, spectrophotometric reflectance (at 560 nm) of the reagent coated film was compared to spectrophotometric reflectance of a freshly made control reagent coated film without oxidizing agents.

Except when the oxidizing agent was a combination of sodium chlorate and benzoyl peroxide, the reagent used in the GOD (glucose oxidase)/PES (phenzine ethosulfate)/MTT analytical system was formulated as follows:
1. 7.5 g of 15% (by weight) aqueous polyvinyl alcohol (88% hydrolyzed, average molecular weight=10,000, a film-forming agent available from Aldrich Chemical Company, Inc.);
2. 4.7 g of 3% (by weight) methyl-hydroxyethyl cellulose in aqueous 0.3M HEPPS buffer;
3. 0.8 g of 5% (by weight) aqueous "TRITON X-100" surfactant;
4. 15 g of the 51.9% (by weight) aqueous silica composition (having the same composition as 4. above in the description of the reagent for the Diaphorase/MTT analytical system); and
5. 4.7 g of "UCAR 455" resin.

The above ingredients were mixed and the pH was adjusted to 8.0 by the addition of sodium hydroxide, thereby resulting in a mixture. The following components were added to 22 g of the resulting mixture: 1.9 g oxidizing agent (added first), 120 mg GOD, 44 mg PES, and 17 mg MTT, thereby yielding wet reagent. (GOD was from BMB Research and contained 202 Units of enzyme per mg of material.) The wet reagent was coated onto a titanium dioxide reflectance film as in the other reagent coated films and dried in the same manner as the other reagent coated films. Comparisons of the reagent coated film with a control reagent coated film were made as described above for the other films. (Also, as shown in Table 1, some of the reagent coated films were aged 4 or 5 days and then compared to a freshly made control reagent coated film.)

When the oxidizing agent was a combination of sodium chlorate and benzoyl peroxide, the reagent used in the GOD/PES/MTT analytical system was formulated as follows:
1. 10.00 g of 15% (by weight) aqueous polyvinyl alcohol (88% hydrolyzed, average molecular weight=10,000, a film-forming agent available from Aldrich Chemical Company, Inc.);
2. 6.20 g of 3% (by weight) methyl-hydroxyethyl cellulose in aqueous 0.3M HEPPS buffer;
3. 1.05 g of 5% (by weight) aqueous "TRITON X-100" surfactant;
4. 20.05 g of the 51.9% (by weight) aqueous silica composition (having the same composition as 4. above in the description of the reagent for the Diaphorase/MTT analytical system); and
5. 6.26 g of "UCAR 455" resin.

The above components were mixed and the pH of the mixture was adjusted to 7.9 by adding sodium hydroxide. To 19.74 g of the resulting pH 7.9 mixture were added 109.58 mg GOD, and 40.9 mg PES. These contents were mixed, thereby resulting in a slurry. To 2.47 g of the resulting slurry were added 0.23 g sodium chlorate, 0.23 g benzoyl peroxide, and 13.8 mg MTT. (Sodium chlorate and benzoyl peroxide were added before MTT was added.) Mixing these components resulted in wet reagent. Wet reagent was coated and dried onto the titanium dioxide film (as described above). After aging 5 days, spectrophotmetric reflectance (at 560 nm) of the reagent coated film was compared to the spectrophotometric reflectance (at 560 nm) of a freshly made control reagent coated film.

The reagent coated transmission film for the GOD/PES/MTT analytical system was formulated as follows:
1. 5.10 g of "UCAR 455" resin;
2. 0.26 g of 5% (by weight) methyl-hydroxyethyl cellulose in aqueous 0.3M HEPPS buffer;
3. 0.27 g of 5% (by weight) aqueous "TRITON X-100" surfactant;
4. 0.24 g of 5% (by weight) aqueous sulfated ethoxylated alcohol derivatives, ammonium salt, an anionic surfactant sold under the trademark "ALFONIC 1412A", available from Vista Chemical Company;
5. 0.11 g of 5% (by weight) aqueous nonionic silicone glycol copolymer, a nonionic surfactant sold under the trademark "DOW CORNING 193".

The pH of the above mixture was adjusted to pH=7.1±0.1 by the addition of dilute hydrochloric acid, thereby forming a resulting mixture.

To the resulting mixture was added 0.50 milliliters (ml) of 1.3M aqueous solution of oxidizing agent (cobalt (II) chloride, stannic chloride, rhodium (III) trichloride hydrate, or saturated nickel acetylacetonate). These contents were mixed on a Heidolph mixer at 500 revolutions per minute (rpm), thereby forming a mixture containing oxidizing agent.

In a separate beaker, 0.8 g methyl ethyl ketone was combined with 0.4 g methanol. (In transmission films that included cobalt (II) chloride or rhodium (III) trichloride hydrate, from about 1.65 g to about 2.65 g water was added to the combination of methyl ethyl ketone and methanol.) Next, 14 mg PES and 104 mg MTT were added, thereby forming a solution.

Next, the solution and the mixture containing oxidizing agent were combined and mixed for about 20 minutes by magnetic stirring, thereby forming the penultimate mixture.

In another beaker, 59 mg GOD was mixed by magnetic stirring with 0.6 g water until the GOD dissolved.

The GOD solution was added to the penultimate mixture. These contents were mixed on a Heidolph mixer at 500 rpm for 1 minute, thereby forming the ultimate mixture. The ultimate mixture was coated at 150 um thickness with a blade coater onto a transparent piece of plastic, which is sold under the trademark "CRONAR", available from DuPont. The resulting wet reagent coated film was dried at 52° C. for 15 minutes.

The dried, reagent coated transmission films containing stannic chloride or rhodium (III) trichloride hydrate remained bright yellow colored after 15 days at room temperature and in the open atmosphere, i.e., no blank reaction was observed. The dried reagent coated transmission films containing nickel acetylacetonate showed a slight blank reaction after 14 days at room temperature and in the open atmosphere, i.e., these films became slightly greenish yellow in color. The dried, reagent coated transmission films containing cobalt (II) chloride showed a blank reaction after 15 days at room temperature and in the open atmosphere, i.e., these films became lime green in color.

The aqueous reagent for the GOD/PES/MTT analytical system was formulated as follows:

5 drops (delivered by a polyethylene plastic disposable transfer pipet from Fisher Scientific (Catalog No. 13-711-5A)) of oxidizing agent were added to 45 mg MTT, 25 mg GOD, and 5 mg PES in a spot plate. Water was added to these contents in an amount sufficient to fill the spot.

After 1 hour at room temperature, the spots were visually observed, and were compared to controls that included no oxidizing agent. The controls were olive green in color. The spots containing t-butylperoxyacetate (sold under the trademark "TRIGONOX F-C50", available from Noury Chemicals, 300 South Wacker Drive, Chicago, Ill. 60606) were yellow in color, indicating a stabilized reagent. The spots containing t-butylperbenzoate (sold under the trademark "TRIGONOX C", available from Noury Chemicals) were slightly greenish yellow in color, indicating some reagent stabilization with t-butylperbenzoate, but less than the stabilization observed with t-butylperoxyacetate.

Unless stated otherwise (in Table 1 and in the above description of Table 1), blank reaction comparisons were made with freshly made aqueous reagent and reagent coated films and freshly made aqueous control reagents and control reagent coated films. Table I shows that in some cases spectrophotometric measurements were not made. Rather, visual comparisons were made on the basis that greater visually observed color change of a film or aqueous reagent meant greater blank reaction had occurred.

As shown above, the reagents utilized in achieving the results shown in Table 1 included a buffer, such as HEPPS, and a surfactant, such as TRITON X-100. If included in the reagent, the buffer should of sufficient type and in sufficient amount to provide a pH in the assay wherein the enzyme will catalyze the reaction involving enzyme, analyte, and mediator. The surfactant, if included in the reagent, should be of sufficient type and in sufficient amount to wet a fluid sample upon addition of the fluid sample to a reagent coated film.

Of the tetrazolium salts tested, MTT is the most prone to a blank reaction. TNBT and INT have greater stability than MTT. It should also be noted the nickel acetylacetonate, stannic chloride, and rhodium (III) trichloride hydrate were included in reagent coated transmission films at a concentration of about 0.09 millimoles (mmol) per gram (g) of wet reagent. All other oxidizing agents referred to in Table 1 were effective in decreasing blank reactions in concentration ranges from about 0.4 to about 2.4 mmol per g of wet reagent.

Table 2 (below) shows that certain oxidizing agents were either ineffective in reducing the blank reaction or were deleterious to the reagent. The results shown in Table 2 were achieved by conducting experiments like those experiments shown in Table 1. Most interesting was the result obtained by using potassium bromate as an oxidizing agent. Bromate and chlorate have similar strengths as oxidizing agents. However, as shown in Table 1, chlorate is quite effective at stabilizing a reagent that includes a tetrazolium salt. Also, in GOD films the possibility of reaction of the oxidizing agent with PES (the mediator) must always be considered. For example, when urea hydrogen peroxide was utilized in the reagent, a red color was produced in the reagent mixture which may have been the result of a reaction of urea hydrogen peroxide with PES.

TABLE 2

INEFFECTIVE OXIDIZING AGENTS

| Oxidizing Agent | Effect on Reagent |
|---|---|
| GOD/PES/MTT (Reflectance Film) | |
| Sodium Lignin Sulfonate | Turned reagent black |
| Urea Hydrogen Peroxide | weak glucose response |
| N-Bromosuccinimide | no glucose response |
| Sodium Borate | polymerized reagent emulsion |
| GDH/NAD/DIAPHORASE/MTT (Reflectance Film) | |
| Potassium Bromate | no decrease in blank reaction |

The present inventive reagent may be utilized to perform an assay of an analyte from a fluid sample, An assay may be conducted by performing the following steps:

a. forming a test sample by combining a fluid sample with the inventive reagent (including the appropriate enzyme for catalytic reaction of the analyte);

b. incubating the test sample;

c. measuring spectrophotometric absorbance, reflectance, or transmittance (whichever is appropriate) of the incubated test sample; and d. correlating the spectrophotometric measurement to the concentration of (or detection of) analyte in the fluid sample.

When glucose was the analyte being measured, reactions were largely complete within about 15–20 seconds following addition of the fluid sample to the reagent. (In the diaphorase/MTT analytical system shown in Table 1, NADH was added to the reflectance film in order to reduce the tetrazolium salt to its formazan, thereby serving as a surrogate assay for glucose.) Glucose assays performed with the present inventive reagent yield a higher final percent reflectance (when reflectance films are used) than when the reagent does not include an oxidizing agent. This decrease in assay sensitivity is beneficial in a glucose assay because it provides a broader analytical range for determining glucose. (For a glucose assay, the dose response curve is usually too steep when performing an assay with a reflectance film that includes a tetrazolium salt.)

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

I claim:

1. A reagent for the assay of an analyte from a fluid sample, comprising:

an enzyme, a mediator, a tetrazolium salt, and at least one oxidizing agent, the enzyme being of sufficient type and in sufficient amount to catalyze a reaction involving enzyme, analyte, and mediator, the mediator being of sufficient type and in sufficient amount to catalyze reduction of the tetrazolium salt, the tetrazolium salt being of sufficient type to be reduced to a colored formazan, and being in sufficient amount to correlate the concentration of formazan to the concentration of analyte in the fluid sample, and the oxidizing agent being selected from the group consisting of sodium chlorate, 2,5-dimethylhexane-2,5-dihydroperoxide, benzoyl peroxide, t-butyl peroxide, sodium iodate, N-ethylmaleimide, t-butylperoxyacetate, nickel acetylacetonate, stannic chloride, rhodium (III) trichloride hydrate, and t-butylperbenzoate, the oxidizing agent further being in sufficient amount to decrease the presence of formazan in the reagent prior to combining the fluid sample and the reagent.

2. The reagent of claim 1, further comprising:

water in sufficient amount to form a solution.

3. The reagent of claim 1, further comprising:

a film-forming agent in sufficient amount to form a cohesive film.

4. The reagent of claim 2, wherein the oxidizing agent is selected from the group consisting of sodium chlorate, benzoyl peroxide, 2,5-dimethylhexane-2,5-dihydroperoxide, and t-butyl peroxide.

5. The reagent of claim 3, wherein the oxidizing agent is selected from the group consisting of sodium chlorate, benzoyl peroxide, 2,5-dimethylhexane-2,5-dihydroperoxide, and t-butyl peroxide.

6. The reagent of claim 2, further comprising:

a buffer of sufficient type and in sufficient amount to provide a pH in the assay wherein the enzyme will catalyze the reaction involving enzyme, analyte, and mediator.

7. The reagent of claim 3, further comprising:

a buffer of sufficient type and in sufficient amount to provide a pH in the assay wherein the enzyme will catalyze the reaction involving enzyme, analyte, and mediator.

8. The reagent of claim 7 further comprising:

a surfactant of sufficient type and in sufficient amount to wet the sample upon addition of the fluid sample to the film.

9. The reagent of claim 3, wherein the amount of oxidizing agent is from about 0.4 to about 2.4 millimoles per gram of wet reagent and the oxidizing agent is not nickel acetylacetonate, stannic chloride, or rhodium (III) trichloride hydrate.

10. The reagent of claim 3, wherein the amount of oxidizing agent is about 0.09 millimoles per gram of wet reagent and the oxidizing agent is selected from the group consisting of nickel acetylacetonate, stannic chloride, and rhodium (III) trichloride hydrate.

11. A reagent for the assay of glucose from a fluid sample, comprising per gram of wet reagent:

a. about 0.39 grams film-forming agent;

b. about 0.23 grams buffer;

c. about 40 milligrams surfactant;

d. about 11 milligrams sodium chloride;

e. about 2.8 milligrams glycerol;

f. about 0.26 grams sodium chlorate, 2,5-dimethylhexane-2,5-dihydroperoxide, benzoyl peroxide, t-butyl peroxide, sodium iodate, N-ethylmaleimide, t-butylperoxyacetate, or t-butylperbenzoate;

g. about 7.3 milligrams glucose dehydrogenase;

h. about 5.9 milligrams diaphorase;

i. about 15 milligrams nicotinamide adenine dinucleotide;

j. about 31 milligrams tetrazolium salt.

12. A reagent for the assay of glucose from a fluid sample, comprising per gram of wet reagent:

a. about 0.47 grams film-forming agent;

b. about 0.29 grams buffer;

c. about 50 milligrams surfactant;

d. about 0.17 grams sodium chlorate, 2,5-dimethylhexane-2,5-dihydroperoxide, benzoyl peroxide, t-butyl peroxide, sodium iodate, N-ethylmaleimide, t-butylperoxyacetate, or t-butylperbenzoate;

e. about 11 milligrams glucose oxidase;

f. about 4.1 milligrams phenazine ethosulfate;

g. about 1.6 milligrams tetrazolium salt.

13. A method of making a stable reagent for the assay of an analyte from a fluid sample, comprising the step of:

combining a reagent that includes an enzyme, a mediator, and a tetrazolium salt capable of being reduced to a formazan with an oxidizing agent selected from the group consisting of sodium chlorate, 2,5-dimethylhexane-2,5-dihydroperoxide, benzoyl peroxide, t-butyl peroxide, sodium iodate, N-ethylmaleimide, t-butylperoxyacetate, nickel acetylacetonate, stannic chloride, rhodium (III) trichloride hydrate, t-butylperbenzoate, the oxidizing agent further being in sufficient amount to decrease the presence of formazan in the reagent prior to combining the fluid sample and the reagent.

14. The method of claim 13, wherein the amount of oxidizing agent is from about 0.4 to about 2.4 millimoles per gram of wet reagent and the oxidizing agent is not nickel acetylacetonate, stannic chloride, or rhodium (III) trichloride hydrate.

15. The method of claim 13, wherein the amount of oxidizing agent is about 0.09 millimoles per gram of wet reagent and the oxidizing agent is selected from the group consisting of nickel acetylacetonate, stannic chloride and rhodium (III) trichloride hydrate.

16. A method of assaying an analyte from a fluid sample, comprising the steps of:

a. forming a test sample by combining the fluid sample with the reagent of claim 2;

b. incubating the test sample;

c. measuring spectrophotometric absorbance of the incubated test sample; and d. correlating the spectrophotometric absorbance measurement to the concentration of analyte in the fluid sample.

17. The method of claim 16, wherein the reagent is the reagent of claim 4.

18. A method of assaying an analyte from a fluid sample, comprising the steps of:

a. forming a test sample by combining the fluid sample with the reagent of claim 3;

b. incubating the test sample;

c. measuring spectrophotometric reflectance or transmittance of the incubated sample;

d. correlating the spectrophotometric reflectance or transmittance measurement to the concentration of analyte in the fluid sample.

19. The method of claim 18, wherein the reagent is the reagent of claim 5.

20. The method of claim 18, wherein the reagent is the reagent of claim 9.

* * * * *